United States Patent [19]
Wenzel

[11] Patent Number: 5,744,415
[45] Date of Patent: Apr. 28, 1998

[54] RARE EARTH METAL CATALYST FOR OLEFIN POLYMERIZATION

[75] Inventor: Timothy Todd Wenzel, Charleston, W. Va.

[73] Assignee: Union Carbide Chemicals & Plastics Technology Corporation, Danbury, Conn.

[21] Appl. No.: 580,468

[22] Filed: Dec. 28, 1995

[51] Int. Cl.$^6$ ...................................... C08F 4/42
[52] U.S. Cl. .................. 502/121; 526/160; 526/943; 502/117; 502/122; 502/123; 502/126; 502/152; 502/155; 502/156
[58] Field of Search ...................... 502/117, 152, 502/155, 156, 126, 121, 122, 123

[56] References Cited

U.S. PATENT DOCUMENTS

| | | | |
|---|---|---|---|
| 5,066,739 | 11/1991 | Pettijohn et al. | 526/127 |
| 5,109,085 | 4/1992 | Pettijohn et al. | 526/160 |
| 5,145,819 | 9/1992 | Winter et al. | 502/117 |
| 5,182,224 | 1/1993 | Pettijohn | 502/110 |
| 5,182,244 | 1/1993 | Pettijohn | 502/110 |
| 5,232,999 | 8/1993 | Conroy et al. | 502/115 |
| 5,260,244 | 11/1993 | Pettijohn | 502/115 |
| 5,556,997 | 9/1996 | Stricklen et al. | 556/11 |

FOREIGN PATENT DOCUMENTS

| | | |
|---|---|---|
| 2696750 | 4/1994 | France . |
| 641232 | 2/1994 | Japan . |

OTHER PUBLICATIONS

Journal of Organometallic Chemistry 471 (1994) 97–104: "New dinuclear bis(cyclopentadienyl)lanthanoid chlorides containing η–$C_5H_4$ ligands linked by a metal–coordinated 2,6-dimethylenepyridyl unit", Gino Paolucci et al.

J. Chem. Soc., Chem Commun. 1990, 880, "Synthesis of Bis(2–methoxyethyl cyclopentadienyl) Complexes of Early Lanthanide Chlorides and the X–Ray Structure of the Lanthanum Complex", Daoli Deng, et al.

Journal of Organometallic Chemistry, 445 (1993) 79–84, "Studies on organolanthanide complexes: XLVI. Synthesis and characterization of N–containing ring–linked biscyclopentadienyl lanthanide and yttrium chlorides", Changtao Qian et al.

Journal of Organometallic Chemistry 466 (1994) 95–100 "Studies on organolanthanide complexes: XLVII. Syntheses of bis(2–methoxyethylcyclopentadienyl)lanthanide tetrahydroborates (Ln=La, Pr, Nd, Sm or Gd); Crystal structures of bis(2–methoxyethylcyclopentadienyl) praseodymium and neodymium tetrahydroborates" Daoli Deng, et al.

Inorg. Chem 1994, 33, 3382–3388 "Studies on Organolanthanide Complexes. 53. Effect of Rare Earth Metal Radius on the Molecular Structure: Synthesis and X–ray Crystal Structure of Bis(2–methoxyethyl)cyclopentadienyl) Rare Earth Metal Chlorides", Changtao Qian et al.

J. Chem. Soc. Dalton Trans. 1994, 1599 "Studies on Organolanthanide Complexes. Part 55. Synthesis of Furan- –bridged Bis(cyclopentadienyl) Lanthanide and Yttrium Chlorides, and Ligand and Metal Tuning of Reactivity of Organolanthanide Hydrides (in situ)", Changtao Qian et al.

Journal of Organometallic Chemistry 466 (1994) 101–105 "Studies on organolanthanide complexes: LIV. Syntheses and X–ray crystal structures of bis(2–methoxyethylcyclopentadienyl) rare earth iodides $(MeOCH_2CH_2C_5H_4)_2LnI$ (Ln=La or Y)," Changtao Qian, et al.

Organometallics 1991, 10, 215–219, "Organometallic Compounds of the Lanthanides. 59. (1,1'–(3–Oxapentamethylene)dicyclopentadienyl)yttrium and –lutetium 3,5–Dimethylpyrazolates. X–ray Crystal Structure of $[O(CH_2CH_2C_5H_4)_2Ln(\mu-N_2C_3HMe_2)(\mu-OH)Ln(C_5H_4CH_2CH_2)_2O](Ln=Y, Lu)$" Herbert Schumann, et al.

Journal of Organometallic Chemistry, 323 (1987) 285–294 "Studies on Organolanthanide Complexes: XII. Synthesis, Identification and Reactivity of Organolanthanide and — Yttrium Chlorides with the Chelatig 1,1'–(3–Oxa–Pentamethylene)Dicyclopentadienyl Ligand", Changtao Qian, et al.

Olonde et al., "Ethylene Polymerization on Neodymium–Metallocene Based Catalysts", an abstract of a presentation at the Rare Earths '92 in Kyoto Conference. 1992.

Pettijohn, et al., "Rare Earth Metallocene Polymerization Catalysts", Metcon '93, Houston, Texas (May 1993).

*Primary Examiner*—David W. Wu
*Attorney, Agent, or Firm*—S. H. Hegedus

[57] ABSTRACT

A catalyst composition comprising: a) (i) a catalyst containing at least one cycloalkadienyl ligand substituted with at least one electron donor residue and coordinated with a metal selected from the group consisting of scandium, yttrium, and lanthanide metals; or (ii) a catalyst containing two cycloalkadienyl ligands coordinated with a metal selected from the group consisting of scandium, yttrium, and lanthanide metals, said cycloalkadienyl ligands connected by a bridging group comprising at least one Group IVA element and at least one electron donor residue; and b) an activating cocatalyst of the formula $R_xM'$, wherein R is alkyl, aryl, or hydride; M' is a Group I, II, or IIIA metal or a Group I, II, or IIIA metal complexed with oxygen, nitrogen, or a halide; and x is equal to the valence of M'.

5 Claims, No Drawings

RARE EARTH METAL CATALYST FOR OLEFIN POLYMERIZATION

This invention relates to the production of olefin polymers using a catalyst composition comprising a rare earth metal catalyst containing one or more cycloalkadienyl ligands substituted with an electron donor residue or two cycloalkadienyl ligands connected by a bridging group that contains an electron donor residue, and a Group I, II, or IIIA metal activating cocatalyst.

BACKGROUND

Certain catalysts containing cyclopentadienyl ligands, rare earth metals, and electron donors are known to polymerize olefin monomers. For example, U.S. Pat. No. 5,109,085 and Pettijohn et al., "Rare Earth Metallocene Polymerization Catalysts," a paper presented at Metcon '93 in Houston, Tex. (May, 1993), describe olefin polymerization catalyst systems comprising a catalyst having the formula $CP_nMX_{4-n} \cdot M'L_x$, wherein Cp is a cyclopentadienyl ligand, M is a metal having an atomic number in the range of 58 to 71, M' is an alkali metal, L is an electron donor ligand, and X is a halogen, along with a cocatalyst comprising an alkali or alkaline earth metal alkyl. These references describe the use of such catalyst systems in solution or slurry phase polymerization to generate olefin polymers of narrow molecular weight distribution.

Although cyclopentadienyl ligand/rare earth metal catalysts have demonstrated good polymerization activity, catalysts of this type are highly electrophilic and undergo destructive C—H activation, in which the rare earth metal center of the catalyst attacks the cyclopentadienyl ligand or the allylic hydrogen of a comonomer. To prevent this, workers in the art typically have loaded the cyclopentadienyl ligand with sterically bulky groups. For instance, Olonde et al., "Ethylene Polymerization on Neodymium-Metallocene Based Catalysts," an abstract of a presentation at the "Rare Earths '92 in Kyoto" Conference (Kyoto, Japan) describes the use of $CP^*_2NdCl_2Li(OEt_2)_2$ with LiR or $MgR_2$ as a catalyst composition for ethylene polymerization, in which Cp* is pentamethylcyclopentadienyl. However, use of bulky ligands like pentamethylcyclopentadienyl on such catalysts tends to lessen their ability to incorporate comonomers effectively.

Paolucci et al., *J. Organomet. Chem.*, 471:97–104 (1994) describes the synthesis of certain bis(cyclopentadienyl) lanthanoid chlorides in which the cyclopentadienyl ligands are linked by a 2,6-dimethylenepyridyl group. The publication states that such compounds "may have catalytic applications (olefin hydrogenation or polymerization)." However, no further information is given on these applications, such as appropriate cocatalysts or reaction conditions.

It has now been discovered that olefin polymers may be produced using a catalyst composition comprising: a) a rare earth metal/cycloalkadienyl ligand catalyst in which an electron donor residue is attached directly to the cycloalkadienyl ligand or is attached to a bridging group connecting two cycloalkadienyl ligands, and b) an activating cocatalyst containing a Group I, II, or IIIA metal. The above catalyst is advantageously less electrophilic and therefore less prone to C—H activation than conventional cyclopentadienyl ligand/rare earth metal catalysts, yet allows comonomers sufficient access to the active metal center.

SUMMARY OF THE INVENTION

The invention provides a catalyst composition for the polymerization of olefins, which comprises: a) a catalyst containing at least one cycloalkadienyl ligand substituted with at least one electron donor residue and coordinated with a metal selected from the group consisting of scandium, yttrium, and lanthanide metals; and b) an activating cocatalyst of the formula $R_xM'$, wherein R is alkyl, aryl, or hydride; M' is a Group I, II, or IIIA metal or a complex of a Group I, II, or IIIA metal with oxygen, nitrogen, or a halide; and x is equal to the valence of M'.

The invention also provides a catalyst composition for the polymerization of olefins, which comprises: a) a catalyst containing two cycloalkadienyl ligands coordinated with a metal selected from the group consisting of scandium, yttrium, and lanthanide metals, said cycloalkadienyl ligands connected by a bridging group comprising at least one Group IVA element substituted with at least one electron donor residue; and b) an activating cocatalyst of the formula $R_xM'$, wherein R is alkyl, aryl, or hydride; M' is a Group I, II, or IIIA metal or a complex of a Group I, II, or IIIA metal with oxygen, nitrogen, or a halide; and x is equal to the valence of M'.

The invention also provides processes for producing olefin polymers by contacting at least one olefin monomer under polymerization conditions with one of the above catalyst compositions.

DETAILED DESCRIPTION OF THE INVENTION

The present catalyst compositions comprise one or more catalysts and one or more activating cocatalysts. Each catalyst contains one or more cycloalkadienyl ligands coordinated with a metal selected from the group consisting of scandium, yttrium, and the lanthanide metals. According to the invention, an electron donor residue is present as a substituent of at least one cycloalkadienyl ligand or is present as a substituent of a bridging group that connects two cycloalkadienyl ligands of the catalyst.

The catalyst may be chosen from a variety of compounds. For example, the catalyst may have one of the following formulas:

  (1)

  (2)

  (3)

In formulas 1, 2, and 3, L is a cycloalkadienyl ligand, such as a cyclopentadienyl, indenyl, or fluorenyl ligand. L may be optionally substituted with one or more alkyl, alkenyl, aryl, or silyl groups containing from about 1 to about 20 carbon atoms. Two L ligands may be connected by a bridging group Q containing one or more Group IVA elements, such as carbon or silicon. Preferably, L is cyclopentadienyl or indenyl. In each of formulas 1, 2, and 3, in addition to any other substituents on the cycloalkadienyl ligands L or the bridging groups Q, one or more electron donor residues are present as a substituents of one or more cyclopentadienyl ligands L or a bridging group Q.

Electron donor residues are functional groups containing electron donor atoms such as oxygen, nitrogen, phosphorus, or other Group VA or VIA elements. Examples of such electron donor residues are alkoxy groups such as methoxy, ethoxy, propoxy and the like, amino groups such as dimethylamino, diethylamino, diphenylamino, and pyridyl, sulfido groups such as alkyl sulfides, and phosphino groups such dialkyl and diaryl phosphines. Preferred electron donor residues are methoxy, dimethylamino, pyridyl, diphenylamino, and diphenylphosphino.

In addition, m is 1 or 2, p is 0 or 1, and p is 0 when m is 1. M is scandium, yttrium, or a lanthanide metal, preferably samarium or neodymium; X is a halide, hydride, aryl, or alkyl; n is equal to the value [3+(the valence of M")−m]; M" is a Group I, II, or IIIA metal, preferably aluminum or lithium; ED is an electron donor ligand; o is an integer from 0 to 4, and R' is alkyl, aryl, or hydride.

The electron donor ligand ED is preferably selected from ethers, esters, ketones, alcohols, amines, organosulfur compounds, and organophosphines. Preferred electron donor ligands are tetrahydrofuran, tetrahydropyran, 1,2-dimethoxyethane, anisole, diethyl ether, di-n-propyl ether, dibutyl ether, methyl t-butyl ether, furan, pyran, dioxane, triethylamine, piperidine, pyridine, methyl formate, ethyl formate, ethyl acetate, butyl acetate, methyl acetate, ethyl anisate, ethylene carbonate, ethyl propionate, dioctyl sulfide, dinaphthylsulfide, triphenylphosphine, and tributylphosphine. Most preferably, the electron donor ligand is tetrahydrofuran, 1,2-dimethoxyethane, anisole, or diethyl ether.

A preferred catalyst is 2-methoxypropano-1,3-bisindenyl samarium (III) chloride ("(BIMP)SmCl"). This catalyst has a bridging group substituted with an electron donor residue:

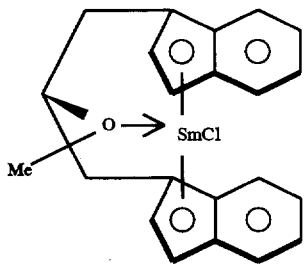

The catalyst may be made by any means and the method of synthesizing it is not critical to the invention. Generally, catalysts of this class are made by reacting a lanthanide trichloride with an anionic form of an electron donor residue-substituted ligand (or the dianionic form thereof if a bridged ligand group is used) in an ether solvent. See for example Qian et al., *J. Organomet. Chem.* 1993, 445: 79–84; Paolucci et al., *J. Organomet. Chem.* 1994, 471:97–104; Qian et al., *J. Chem. Soc. D.A.* 1994, 1599; Qian et al., *Inorg. Chem.* 1994, 33:3382–3388, and references cited therein.

The activating cocatalyst is a compound of the formula:

$R_xM'$, wherein R is alkyl, aryl, or hydride; M' is a Group I, II, or IIIA metal or a Group I, II, or IIIA metal complexed with oxygen, nitrogen, or a halide; and x is equal to the valence of M'.

Examples of suitable activating cocatalysts are dibutyl magnesium, butyl lithium, triisobutyl aluminum, diisobutylaluminum hydride, and methylaluminoxane. Preferably, the activating cocatalyst is an organomagnesium compound, such as dibutyl magnesium.

The mole ratio of metal M' in the activating cocatalyst to metal M in the catalyst is preferably from about 1 to about 1000, more preferably from about 5 to about 20.

The catalyst composition optionally contains an external electron donor as a separate ingredient. Compounds useful as the external electron donor are the same as those suitable as the electron donor ligand. Preferably, the external electron donor is tetrahydrofuran, 1,2-dimethoxyethane, anisole, or diethyl ether.

The mole ratio of external electron donor to catalyst in the catalyst composition is typically from about 5 to about 100, preferably about 5 to about 10.

The catalyst composition may be supported or unsupported, or may be spray dried with or without filler. In the case of a supported catalyst composition, the catalyst composition may be impregnated in or deposited on the surface of an inert support such as silicon dioxide, aluminum oxide, magnesium dichloride, polystyrene, polyethylene, polypropylene, or polycarbonate, such that the catalyst composition is between 1 and 90 percent by weight of the total weight of the catalyst composition and the support. In one embodiment of the invention, an external electron donor may be appended to the support. For instance, polystyrene with appended methoxy groups may be used as the support.

Polymerization may be conducted by any suspension, solution, slurry, or gas phase process, using known equipment and reaction conditions, and is not limited to any specific type of reaction system. Generally, olefin polymerization temperatures range from about 0° C. to about 200° C. at atmospheric, subatmospheric, or superatmospheric pressures. Slurry or solution polymerization processes may utilize subatmospheric or superatmospheric pressures and temperatures in the range of about 40° C. to about 110° C. A useful liquid phase polymerization reaction system is described in U.S. Pat. No. 3,324,095. Liquid phase reaction systems generally comprise a reactor vessel to which olefin monomer and catalyst composition are added, and which contains a liquid reaction medium for dissolving or suspending the olefin polymer. The liquid reaction medium may consist of the bulk liquid monomers or an inert liquid hydrocarbon that is nonreactive under the polymerization conditions employed. Although such an inert liquid hydrocarbon need not function as a solvent for the catalyst composition or the olefin polymer obtained by the process, it usually serves as solvent for the monomers employed in the polymerization. Among the inert liquid hydrocarbons suitable for this purpose are isopentane, hexane, cyclohexane, heptane, benzene, toluene, and the like. Reactive contact between the olefin monomer and the catalyst composition should be maintained by constant stirring or agitation. The reaction medium containing the olefin polymer product and unreacted olefin monomer is withdrawn from the reactor continuously. The olefin polymer product is separated, and the unreacted olefin monomer and liquid reaction medium are recycled into the reactor.

Preferably, gas phase polymerization is employed, with superatmospheric pressures in the range of 1 to 1000 psi, preferably 50 to 400 psi, most preferably 100 to 300 psi, and temperatures in the range of 30° to 130° C., preferably 65° to 110° C. Stirred or fluidized bed gas phase reaction systems are particularly useful. Generally, a conventional gas phase, fluidized bed process is conducted by passing a stream containing olefin monomer continuously through a fluidized bed reactor under reaction conditions and in the presence of catalyst composition at a velocity sufficient to maintain a bed of solid particles in a suspended condition. A stream containing unreacted monomer is withdrawn from the reactor continuously, compressed, cooled, optionally partially or fully condensed (such as described in U.S. Pat. Nos. 4,528,790; 5,462,999; and 5,453,471), and recycled into the reactor. Product is withdrawn from the reactor and make-up monomer is added to the recycle stream. As desired for temperature control of the system, any gas or liquid inert to the catalyst composition and reactants may also be present in the gas stream. In addition, a fluidization aid such as carbon black, silica, clay, or talc may be used, as disclosed in U.S. Pat. No. 4,994,534.

The molecular weights of olefin polymers made from the catalyst composition of the invention are particularly sensitive to changes in temperature. In gas phase polymerization, individual particles of growing polymer may undergo larger temperature swings than in slurry reactors. Thus the molecular weight distributions of the resulting olefin polymers may be greater when made in the gas phase, advantageously resulting in products that are particularly easy to process, for example by extrustion.

Polymerization may be carried out in a single reactor or in two or more reactors in series, and is conducted substantially in the absence of catalyst poisons. Organometallic compounds may be employed as scavenging agents for poisons to increase the catalyst activity. Examples of scavenging agents are metal alkyls, preferably aluminum alkyls, most preferably triisobutylaluminum. Use of such scavenging agents is well known in the art.

Other conventional additives may be included in the process, provided they do not interfere with functioning of the catalyst composition.

When hydrogen is used as a chain transfer agent in the process, it is used in amounts varying from about 0.00001 to about 10 moles of hydrogen per mole of total monomer feed. Alkyl silanes (e.g., $PhSiH_3$) may also be used as chain transfer agents.

Olefin polymers produced according to the invention are olefin homopolymers, copolymers and higher interpolymers with densities ranging from about 0.86 to about 0.95. Olefin monomers such as ethylene or linear or branched higher alpha-olefins containing 3 to about 20 carbon atoms, for example, propylene, 1-butene, 1-pentene, 1-hexene, 4-methyl-1-pentene, 1-octene, and 3,5,5-trimethyl-1-hexene, may be used. Olefin polymers according to the invention may also contain conjugated or non-conjugated dienes, such as linear, branched, or cyclic hydrocarbon dienes having from about 4 to about 20, preferably 5 to 12, carbon atoms. Preferred dienes include 1,3-butadiene, 1,4-pentadiene, 1,5-hexadiene, 5-vinyl-2-norbornene, 1,7-octadiene, vinyl cyclohexene, dicyclopentadiene, butadiene, isoprene, ethylidene norbornene and the like. Aromatic compounds having vinyl unsaturation such as styrene and substituted styrenes, and polar vinyl monomers such as acrylonitrile, maleic acid esters, vinyl acetate, acrylate esters, methacrylate esters, vinyl trialkyl silanes and the like may also be utilized as olefin monomers. Specific olefin polymers that may be made according to the invention include, for example, ethylene copolymers, propylene copolymers, ethylene/propylene rubbers (EPR's), ethylene/propylene/diene terpolymers (EPDM's), and the like.

The following examples further illustrate the invention.

EXAMPLE 1

The catalyst (BIMP) SmCl is prepared as follows.
Preparation of 1,3-bis(3-indenyl)-2-methoxypropane Ligand To a solution of 23.2 g of indene dissolved in 200 mL tetrahydrofuran chilled to −78° C. under argon was added 80 mL of butyl lithium (2.5M in hexanes). The resulting solution was warmed to room temperature for one hour and then re-chilled to −78° C. To this solution was added 13.7 g epibromohydrin. After stirring for one hour at −78° C., the solution was brought to room temperature for one hour and then refluxed for one hour. After cooling, 12.6 g of dimethyl sulfate was added and this mixture was refluxed for 48 hours. Hexane and saturated ammonium chloride were then added and the organic layer recovered. After further washing the organic layer with brine, it was dried over $MgSO_4$ and evaporated to an oil. A portion of this oil was chromatographed to provide 1,3-bis(3-indenyl)-2-methoxypropane as a pale yellow oil.

Preparation of Samarium Complex of 1,3-bis(3-indenyl)-2-methoxypropane

To a solution of 1,3-bis(3-indenyl)-2-methoxypropane in tetrahydrofuran is added two equivalents of n-butyllithium at −78° C. The resulting mixture is warmed to room temperature for one hour. The mixture is then chilled to −78° C. and one equivalent of $SmCl_3$ is added in portions. The resulting mixture is evaporated and extracted with diethyl ether, which is evaporated to give impure (BIMP)SmCl.

EXAMPLE 2

A mixture of (BIMP)SmCl as prepared in Example 1 and dibutyl magnesium cocatalyst is combined into a catalyst composition and used to polymerize ethylene and 1-hexene as follows.

A solution of catalyst and dibutyl magnesium cocatalyst in dry toluene is first stirred for 30 minutes. The resulting catalyst composition is injected into a slurry phase reactor consisting of a one liter, stainless steel autoclave equipped with a mechanical agitator after it has been purged with nitrogen/oxygen-free hexane and charged with 1-hexene comonomer at 55° C. The reactor is then sealed and heated to 75° C., at which point ethylene is added to achieve a partial pressure of 85 psi. Sufficient ethylene is added during the course of the reaction to maintain that partial pressure. The reactor is then cooled, vented, and opened to recover copolymer product.

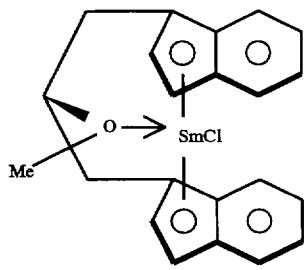

I claim:

1. A catalyst composition for the polymerization of olefins, which comprises:

a) a catalyst having a formula selected from the group consisting of $$Q_pL_mMX_nM''(ED)_o \quad (1)$$

$$[Q_pL_2MR']_2 \quad (2)$$

$$Q_pL_2MR'(ED)_o \quad (3)$$

wherein

Q is a bridging group containing one or more Group IVA elements;
L is a cyclopentadienyl, indenyl, or fluorenyl ligand;
M is scandium, yttrium, or a Lanthanide metal;
X is a halide, hydride, aryl group or alkyl group;
M" is a Group I, II, or IIIA metal;
ED is an electron donor ligand;
R' is an alkyl group, an aryl group, or a hydride;
m is 1 or 2;
p is 0 or 1, and p is 0 when m is 1;
n is equal to the value [3+(the valence of M")−m], and o is an integer from 0 to 4;
wherein an electron donor residue containing at least one Group VA or IVA element is present as a substituent of an L or Q; and b) an activating cocatalyst of the formula $R_xM'$, wherein R is alkyl, aryl, or hydride; M' is a Group I, II, or IIIA metal or a Group I, II, or IIIA metal complexed with oxygen, nitrogen, or a halide; and x is equal to the valence of M'.

2. The catalyst composition of claim 1, wherein the electron donor residue is selected from the group consisting of alkoxy groups, amino groups, sulfido groups, and phosphino groups.

3. The catalyst composition of claim 1, wherein the activating cocatalyst is selected from the group consisting of dibutyl magnesium, butyl lithium, triisobutyl aluminum, diisobutylaluminum hydride, and methylaluminoxane.

4. The catalyst composition of claim 1, further comprising an external electron donor selected from the group consisting of tetrahydrofuran, 1,2-dimethoxyethane, anisole, and diethyl ether.

5. The catalyst composition of claim 1 wherein the catalyst has the formula: